US008895079B2

(12) United States Patent
Wang et al.

(10) Patent No.: US 8,895,079 B2
(45) Date of Patent: Nov. 25, 2014

(54) COMBINATIONS OF BOTANICAL EXTRACTS FOR PROMOTING CARDIOVASCULAR HEALTH

(75) Inventors: Yanwen Wang, Charlottetown (CA); Jeffrey Zidichouski, Charlottetown (CA)

(73) Assignee: National Research Council of Canada, Ottawa (CA)

( * ) Notice: Subject to any disclaimer, the term of this patent is extended or adjusted under 35 U.S.C. 154(b) by 1446 days.

(21) Appl. No.: 12/223,297

(22) PCT Filed: Feb. 9, 2007

(86) PCT No.: PCT/CA2007/000194
§ 371 (c)(1),
(2), (4) Date: Jul. 28, 2008

(87) PCT Pub. No.: WO2007/090289
PCT Pub. Date: Aug. 16, 2007

(65) Prior Publication Data
US 2010/0239603 A1    Sep. 23, 2010

Related U.S. Application Data

(60) Provisional application No. 60/711,455, filed on Aug. 25, 2005.

(51) Int. Cl.
| A61K 38/00 | (2006.01) |
| A61K 36/85 | (2006.01) |
| A61K 36/71 | (2006.01) |
| A61K 36/45 | (2006.01) |
| A61K 36/48 | (2006.01) |
| A61K 45/06 | (2006.01) |
| A61K 31/4745 | (2006.01) |
| A61K 36/06 | (2006.01) |

(52) U.S. Cl.
CPC ............. *A61K 45/06* (2013.01); *A61K 31/4745* (2013.01); *A61K 36/06* (2013.01)
USPC ...... 424/725; 424/195.16; 424/726; 424/732; 424/766; 424/757

(58) Field of Classification Search
None
See application file for complete search history.

(56) References Cited

U.S. PATENT DOCUMENTS

| 5,589,182 | A | 12/1996 | Tashiro et al. |
| 6,239,139 | B1 | 5/2001 | Kim et al. |
| 6,544,525 | B1* | 4/2003 | Yegorova ................. 424/195.16 |
| 6,998,501 | B1* | 2/2006 | Wright et al. ...................... 560/5 |
| 2006/0078531 | A1 | 4/2006 | Sota |
| 2006/0078532 | A1 | 4/2006 | Omoigui |
| 2006/0078533 | A1 | 4/2006 | Omoigui |
| 2006/0223838 | A1* | 10/2006 | Jiang et al. ..................... 514/284 |
| 2006/0275294 | A1 | 12/2006 | Omoigui |

FOREIGN PATENT DOCUMENTS

| CN | 1437973 A | | 8/2003 |
| JP | 01146823 A | * | 6/1989 |
| JP | 09-095452 A2 | | 4/1997 |
| JP | 09-255570 A2 | | 9/1997 |
| JP | 2000-264842 A2 | | 9/2000 |
| JP | 2004-331635 A | | 11/2004 |
| JP | 2008513382 A | | 5/2008 |
| WO | 01/30359 A1 | | 5/2001 |
| WO | WO 01/30359 | | 5/2001 |

OTHER PUBLICATIONS

Targher et al., "Relation of Nonalcoholic Hepatic Steatosis to Early Carotid Atherosclerosis in Health Men" (Diabetes Care, vol. 27, No. 10, Oct. 2004).*
Chan et al. "Hepatic Steaatosis in obese Chinese children" (International Journal of Obesity (2004) 28, pp. 1257-1263.*
European Extended Search Report on European application 07 71 0609.4 mailed Jun. 10, 2009.
European Patent Office document XP002529978, English abstract of JP 09 255570, published Sep. 30, 1997.
Kong W, et al., Nature Medicine, vol. 10, No. 12, pp. 1344-1351, Dec. 1, 2004.
Doggrell SA, Expert Opinion on Investigational Drugs. vol. 14, No. 5, pp. 683-685, May 1, 2005.
Office Action dated Sep. 29, 2011 on corresponding European application 07710609.4.
Heber et al. American Journal of Clinical Nutrition, 1999, vol. 69, pp. 231-236.
Kong et al. Nature Medicine, 2004, vol. 10, No. 12, pp. 1344-1351.
Kong et al. Expert Opinion Investigational Drugs, 2005, vol. 14, No. 5, pp. 683-685.
Office Action on Japanese Patent Application P2008-553588 dated May 15, 2012.

* cited by examiner

*Primary Examiner* — Chris R Tate
*Assistant Examiner* — Deborah Davis
(74) *Attorney, Agent, or Firm* — Laura Catherine Eckenswiller (57) ABSTRACT

A blood lipid lowering agent that functions through a same mechanism as berberine (e.g. berberine, one or more pharmacologically acceptable salts of berberine or a mixture thereof) and a blood lipid lowering agent that functions through a different mechanism than berberine (e.g. phytosterols, phytostanols, esters thereof or mixtures thereof) act synergistically to improve blood lipid profiles, for example, lowering total cholesterol, LDL-C or nonHDL-C, and triglyceride, and increasing the ratio of HDL-C to nonHDL-C. The two may be used in combination to treat or reduce the chance of contracting cardiovascular disease, hyperlipidemia, atherosclerosis, coronary heart disease, angina, cerebrovascular disease, stroke, overweight or obesity, diabetes, insulin resistance, hyperglycemia, hypertension, arrhythmia, diseases of the central nervous system, diseases of the peripheral nervous system and/or inflammation. The blood lipid lowering agent that functions through a same mechanism as berberine, with or without the blood lipid lowering agent that functions through a different mechanism than berberine, may also be used to control weight.

11 Claims, 5 Drawing Sheets

COMBINATIONS OF BOTANICAL EXTRACTS FOR PROMOTING CARDIOVASCULAR HEALTH

CROSS-REFERENCE TO RELATED APPLICATIONS

This application is a National Phase Entry of International Patent Application PCT/CA2007/000194 filed Feb. 9, 2007 and claims the benefit of U.S. provisional patent application U.S. Ser. No. 60/771,455 filed Feb. 9, 2006.

FIELD OF THE INVENTION

The present invention relates to medicinal compositions, particularly to combinations of botanical extracts for promoting cardiovascular health.

BACKGROUND OF THE INVENTION

Cardiovascular disease (CVD), including coronary heart disease, atherosclerosis, stroke, myocardial infarction, sudden death syndrome, is the number one cause of death in most developed countries all over the world. Also, in developing countries, the prevalence of CVD is on the increase and appears to be linked to people adopting a more Westernized (North American) diet (high fat) and lifestyle (sedentary). Elevated circulating cholesterol levels, in particular low-density-lipoprotein cholesterol (LDL-cholesterol) levels, have been well established as one of the major risk factors for the development and progression of CVD. A high level of circulating triglycerides is also a critical risk factor in the increased incidence of CVD. Accordingly, reducing total cholesterol and/or triglyceride levels is advised to high risk patients to reduce cardiovascular-related risk factors that are known and demonstrated to be associated with a higher incidence of morbidity and mortality. Subjects with obesity, diabetes and hyperlipidemia are three major subgroups of the population that are adversely affected by high cholesterol and triglyceride levels.

To date, it is known that plant sterols/stanols and their various analogues can reduce circulating blood cholesterol concentration by inhibiting dietary and biliary cholesterol absorption in the intestine. Red Yeast Rice supplements lower blood cholesterol through inhibiting the activity of the rate-limiting enzyme, HMG-CoA reductase that essentially governs cholesterol biosynthesis in mammals. Berberine was most recently reported to be able to lower blood cholesterol through enhancing cholesterol clearance by increasing LDL-receptor mediated cholesterol clearance. These three types of bioactive compounds (berberine, plant sterols/stanols, and Red Yeast Rice) work through distinct mechanisms.

Presently available products have been demonstrated to work via different mechanisms and achieve the expected results to certain degree; however, the efficacy of presently available products is limited and/or is accompanied by side effects. Statin drugs reduce blood cholesterol through suppressing the activity of HMG-CoA reductase, the rate-limiting enzyme in cholesterol synthesis, but this class of compounds has little or no effect on lowering triglycerides. The major drawback of statin or statin-like compounds is that the synthesis of an important mitochondrial enzyme called Q10 is inhibited, depending on HMG-CoA reductase to be intact and functional. Blockage of HMG-CoA reductase by statins causes reduced coenzyme Q10 levels and this is thought to underlie the cause of a number of statin-associated muscle-related myopathies reported, such as muscle soreness, muscle weakness, muscle tenderness, intense muscle pain, peripheral neuropathy and muscle protein breakdown called rhabdomylosis and may underlie other side effects that are dependent on the presence of normal physiological levels of coenzyme Q10. In particular, rhabdomylosis can be both a serious and a life threatening side effect clearly associated with the use of statin drugs where the muscle breakdown causes major organ damage to both the liver and kidney that has resulted in many reported deaths. The all-cause discontinuation rate of statin use was about 10% and discontinuation because of adverse events was about 4%. Plant sterols and their different analogues inhibit cholesterol absorption and thus reduce cholesterol concentration in the plasma. However, when blood cholesterol concentration is reduced through the inhibition of cholesterol absorption, cholesterol synthesis increases simultaneously as a compensation mechanism to counteract the reduced absorption of dietary and biliary cholesterol. Plant sterols and their different analogues have not previously been shown to have any significant effect in reducing serum triglyceride levels.

A recent discovery of a botanical bioactive alkaloid compound berberine, contained in Chinese Huanglian, goldenseal, or goldthread, lowers cholesterol levels through increasing LDL-receptor mediated cholesterol clearance.

SUMMARY OF THE INVENTION

It has now been found that a blood lipid lowering agent that functions through a same mechanism as berberine and a blood lipid lowering agent that functions through a different mechanism than berberine act synergistically to improve blood lipid profiles. Such improvements may be manifested, for example, in lowering blood lipids such as total cholesterol (T-C), low-density-lipoprotein cholesterol (LDL-C) or non-high-density-lipoprotein cholesterol (nonHDL-C), and/or triglycerides (TG), and/or in increasing the ratio of high-density-lipoprotein cholesterol (HDL-C) to LDL-C or non-HDL-C. Blood lipid modulations (e.g. the lowering effects) of the two administered in combination are more than the sum of the two administered separately.

Thus, in one aspect of the invention, there is provided a blood lipid level lowering composition comprising a blood lipid lowering agent that functions through a same mechanism as berberine, and a blood lipid lowering agent that functions through a different mechanism than berberine.

In a second aspect of the invention, there is provided a use of a blood lipid lowering agent that functions through a same mechanism as berberine and a blood lipid lowering agent that functions through a different mechanism than berberine for lowering blood lipid levels in a mammal.

In a third aspect of the invention, there is provided a use of a blood lipid lowering agent that functions through a same mechanism as berberine and a blood lipid lowering agent that functions through a different mechanism than berberine for manufacturing a medicament for lowering blood lipid levels in a mammal.

In a fourth aspect of the invention, there is provided a commercial package comprising a blood lipid lowering agent that functions through a same mechanism as berberine and a blood lipid lowering agent that functions through a different mechanism than berberine together with instructions for use in lowering blood lipid levels in a mammal.

In a fifth aspect of the invention, there is provided a method comprising administering a blood lipid lowering agent that functions through a same mechanism as berberine and a blood lipid lowering agent that functions through a different mechanism than berberine to a mammal to result in the lowering of blood lipid levels.

In a sixth aspect of the invention, there is provided a use of a blood lipid lowering agent that functions through a same mechanism as berberine for controlling weight of a mammal.

The blood lipid lowering agent that functions through a same mechanism as berberine (hereinafter referred to as "BBR") may be from a naturally occurring source or from a synthetic or semi-synthetic source. BBR in a naturally occurring source may be used "as is", for example, plant material containing the BBR may be used directly. BBR from any source may be subject to one or more isolation or concentration steps (e.g. extraction, crystallization, filtration) to provide a purer and/or more concentrated form of the BBR. Preferably, BBR is used as a crude extract from a natural source, as a concentrated extract from a natural source, as a partially purified extract from a natural source, or in a substantially pure form from a natural, synthetic or semi-synthetic source. BBR may be available commercially from a number of suppliers.

BBR may comprise, for example, berberine, one or more berberine derivatives or analogs, one or more pharmacologically acceptable salts thereof, or a mixture thereof. Berberine is an isoquinoline alkaloid of formula (I):

(I)

Berberine, berberine derivatives or analogs, salts thereof or mixtures thereof may be found in a variety plants, for example *Coptis chinensis* rhizomes (huanglian, *coptis*, goldthread), goldenseal, goldthread, *Phellodendron amurense* bark, *Berberis sargentiana*, *Berberis thunbergii*, *Berberis vulgaris* (Barberry), *Berberis aquifolium* (Oregon grape), *Hydrastis Canadensis* (goldenseal), and *Berberis aristata* (tree turmeric). A recent paper demonstrated that a berberine mixture from goldenseal is more effective than pure berberine chloride alone.

Berberine, berberine derivatives or analogs, and salts thereof may be prepared synthetically or semi-synthetically by a variety of chemical and/or enzymatic methods known in the art, for example, as described in United States patent publication 2006/0223838 published Oct. 5, 2006, the disclosure of which is herein incorporated by reference.

In one embodiment, the BBR comprises berberine, one or more pharmacologically acceptable salts of berberine or a mixture thereof. Preferred pharmacologically acceptable salts of berberine include, for example, acid addition salts, e.g. chlorides, sulfates, carbonates, phosphates, citrates and acetates. Acid addition salts may be produced by reacting berberine with an appropriate acid.

The blood lipid lowering agent that functions through a different mechanism than berberine (hereinafter referred to as "BLLA") may be, for example, a plant sterol (phytosterol), a plant stanol (phytostanol), a statin, an isoflavone, a natural product containing one or more of the above and/or other blood lipid lowering agents, a derivative thereof or a mixture thereof.

In particular, a plant sterol, a plant stanol, an ester of a plant sterol, an ester of a plant stanol or a mixture thereof provide surprisingly synergistic effects when used in conjunction with BBR. Plant sterols comprise alcoholic derivatives of cyclopentanoperhydrophenanthrenes. Plant stanols are saturated forms of the sterols. Some representative examples of plant sterols are beta-sitosterol, campesterol and stigmasterol. Some representative examples of plant stanols are sitostanol and campestanol. Particularly preferred esters of plant sterols or plant stanols are esters with unsaturated fatty acids, for example omega-3 fatty acids (e.g. docosahexaenoic acid (DHA), docosapentaenoic acid (DPA), eicosapentaenoic acid (EPA) and alpha-linolenic acid (ALA)), and esters with any other acids that are suitable for consumption and/or that benefit health (e.g. ascorbic acid). Plant sterols and plant stanols are found in legumes, fruits, vegetables, trees and other plants as well as in fungi and other microorganisms. Plant material containing plant sterols and/or stanols may be used directly, or the plant sterols and/or stanols may be extracted from the plant material and used in a more purified and/or concentrated form. Preferably, plant sterols and plant stanols are extracted from plant or other phytosterol/phytostanol-containing materials. Some examples of plant materials include, for example, soybean oil, tall (pine tree) oil, wood pulp, leaves, nuts, vegetable oils, corn and rice. Plant sterols and plant stanols are available commercially from a number of suppliers.

Some natural products contain a variety of BLLAs. For example, Red Yeast Rice contains several different naturally-occurring statins, including lovastatin, which are naturally produced during the fermentation process involved with producing Red Yeast Rice. However, the active lipid lowering components in Red Yeast Rice are not solely statins since the amount of statins obtained from Red Yeast Rice consumption is much lower than the dose of statin drug. The lipid lowering effect of Red Yeast Rice is more likely a result of the combination of lovastatin with other different statins and isoflavones found in Red Yeast Rice extracts. In addition, Red Yeast Rice is a fermented rice product that has been used in Chinese cuisine and as a medicinal food to promote blood circulation for centuries, without significant side effects that occurs after statin drug supplementation.

Blood lipid levels may include, for example, triglyceride (TG) levels, total cholesterol (T-C) levels and non-high-density-lipoprotein cholesterol (nonHDL-C) levels (e.g. very low-density lipoprotein cholesterol (VLDL-C) levels, intermediate-density lipoprotein cholesterol (IDL-C) levels and/or low-density-lipoprotein cholesterol (LDL-C) levels). Compositions, uses and methods of the present invention may lower one or more of these levels in the blood. The lowering of blood lipid levels may be measured in whole blood, blood plasma and/or blood serum.

BBR and BLLA are used in amounts effective to provide a daily dose of the combination of ingredients that lowers blood lipid levels. For example, the daily dose of each ingredient may in some cases be 5 mg or more per kg of body weight of a subject. In other cases, doses of each ingredient of 10 mg or more per kg of body weight may be appropriate. In yet other cases, doses of each ingredient of 50 mg or more per kg of body weight may be appropriate. For an 80 kg subject, a dose of each ingredient of 10 mg or more per kg of body weight is about 0.8 grams or more of each ingredient per day. Daily dosages can be given all at once in a single dose or can be given incrementally in several smaller dosages. Thus, the composition of the present invention can be formulated such that the recommended daily dose is achieved by the administration of a single dose or by the administration of several smaller doses.

BBR and BLLA may be used for any suitable length of time to reduce blood lipid levels in the subject. Preferably, BBR and BLLA are used for at least two weeks. Longer periods of usage can provide greater reduction in blood lipid levels and are envisaged as continued use of all known lipid control therapeutic approaches is required to effectively control or maintain lower lipid levels in the long term. For example, discontinuation of statin therapy results in blood lipid profiles returning to pre-intervention levels.

BBR and BLLA may be formulated in a dosage form. Dosage forms include powders, tablets, capsules, softgels, solutions, suspensions, emulsions and other forms that are readily appreciated by one skilled in the art. The compositions may be administered orally, parenterally, intravenously or by any other convenient method. Oral administration is preferred.

BBR and BLLA may be administered simultaneously or within a short period of time of one another. Preferably, BBR and BLLA are administered simultaneously. If they are administered within a short period of time of one another, the period time should not be so long that the synergistic effect of BBR and BLLA is not realized.

BBR and BLLA may be formulated together with other pharmacologically acceptable ingredients typically used in the nutraceutical and/or pharmaceutical compositions, for example antiadherents, binders (e.g. starches, sugars, cellulose, hydroxypropyl cellulose, ethyl cellulose, lactose, xylitol, sorbitol and maltitol), coatings (e.g. cellulose, synthetic polymers, corn protein zein and other polysaccharides), disintegrants (e.g. starch, cellulose, cross-linked polyvinyl pyrrolidone, sodium starch glycolate and sodium carboxymethyl cellulose), fillers/diluents (e.g. water, plant cellulose, dibasic calcium phosphate, vegetable fats and oils, lactose, sucrose, glucose, mannitol, sorbitol and calcium carbonate), flavors and colors, glidants, lubricants (e.g. talc, silica, vegetable stearin, magnesium stearate and stearic acid), preservatives (e.g. vitamin A, vitamin E, vitamin C, selenium, cysteine, methionine, citric acid, sodium citrate, methyl paraben and propyl paraben), antioxidants, sorbents, sweeteners, and mixtures thereof.

BBR and BLLA may also be admixed with a food or beverage and taken orally in such a manner. Fortified foods and beverages may be made by adding BBR and BLLA during the manufacturing of the food or beverage. Alternatively, the consumer may add BBR and BLLA to the food or beverage near the time of consumption. Each ingredient may be added to the food or beverage together with the other ingredients or separately from the other ingredients. Examples of foods and beverages are, but not limited to, cereals, snack bars, dairy products, fruit juices, powdered food and dry powder beverage mixes.

BBR and BLLA may be packaged together in a commercial package together with instructions for their use. Such packages are known to one skilled in the art and include, for example, bottles, jars, blister packs, boxes, etc.

BBR and BLLA may be used to treat or reduce the chance of contracting or the progression of a number of diseases or conditions in a subject. Diseases or conditions include, for example, cardiovascular disease, hyperlipidemia, atherosclerosis, coronary heart disease, angina, cerebrovascular disease, stroke, overweight or obesity, diabetes, insulin resistance, hyperglycemia, hypertension, arrhythmia, diseases of the central nervous system, diseases of the peripheral nervous system and inflammation. BBR and BLLA are particularly effective at preventing cardiovascular diseases, for example, coronary heart disease, atherosclerosis, stroke, arrhythmia, myocardial infarction and sudden death syndrome. BBR and BLLA may also be used to control weight in a subject.

Subjects are humans and animals with blood circulatory systems, particularly mammals, for example, humans, dogs, cats, horses and rodents (e.g. hamsters, mice and rats).

Without being held to any particular mechanism of action, synergy between BBR and BLLA is thought to arise by affecting two or more blood lipid control mechanisms to achieve a blood lipid-lowering efficacy greater than the additive effect. BBR and BLLA also provide an anti-inflammatory effect that provides additional health benefits and protection, especially to the cardiovascular system. In addition to the synergistic effect, there is a reduction in side effect profile compared to targeting a single mechanism. For example, BBR and BLLA may simultaneously affect three independent pathways to synergistically lower serum cholesterol levels, lower triglycerides and reduce or down-regulate chronic inflammatory mechanism.

Circulating cholesterol concentration is a function of input from absorption (dietary and biliary cholesterol) and de novo synthesis relative to clearance through hepatic and non-hepatic removal mechanisms as well as cholesterol elimination through excretion. There are three major pathways involved in controlling cholesterol homeostasis in the human body. Many of the available natural products that lower body cholesterol target a single distinct pathway and either show limited efficacy or require a high dose level to control cholesterol. Currently there is a high consumer demand for a novel product that can significantly reduce cholesterol levels at a reasonable daily dose and without causing significant side effects. Embodiments of the present invention can meet this demand.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

An objective of the following examples was to show that a combination of BBR and BLLA results in a synergistic improvement in blood lipid profile than each intervention on its own, toward positive health benefits to the cardiovascular system, cerebrovascular vasculature, liver, and body weight.

Materials:

Table 1 lists materials used in the following examples.

TABLE 1

| Material | Source |
| --- | --- |
| Berberine chloride (BBRCl) | Sigma-Aldrich Co., purity >98% |
| Plant stanols (PS) | Forbes-Medi Tech Inc., purity >92%* |
| Casein | MP Biomedicals |
| Corn starch | MP Biomedicals |
| Sucrose | MP Biomedicals |
| Cholesterol | MP Biomedicals |
| Male Golden Syrian Hamsters | Charles River Co. |
| Male Sprague-Dawley rats | Charles River Co. |

*Plant stanols (PS) consist of 10% campestanols and 82% sitostanols, with overall 92% of plant stanols.

Example 1

This example provides data for the combination of berberine chloride (BBRCl) with plant stanols (PS) to improve blood lipid profiles toward positive health benefits to the cardiovascular system, cerebrovascular system, vasculature, liver, and body weight.

A controlled, four week animal study was performed to compare and contrast the effects of three interventional strategies on blood cholesterol and triglyceride levels. Four randomized groups of 15 male Golden Syrian hamsters were fed isocaloric diets as follows:

Control a semi-synthetic casein-corn starch-sucrose diet that contained 0.15% (w/w) cholesterol and 5% (w/w) fat BBRCl control diet containing 100 mg/kg·d of BBRCl PS control diet containing 1% (w/w) PS BBRCl+PS control diet containing 100 mg/kg·d BBRCl and 1% (w/w) PS BBRCl and PS were introduced into the diet by blending. The primary endpoint at the end of the study was to determine the effects of each intervention on circulating blood lipids including total cholesterol (T-C), high-density-lipoprotein cholesterol (HDL-C), nonHDL-C (which is indicative of LDL-C levels) and triglyceride (TG) profiles. All lipids were measured by the standard enzymatic method.

The hamster has been established as a good model for studying human cholesterol metabolism and was used to examine the effects of BBRCl and plant stanols each alone and in combination on circulating blood lipid levels. As well, tissues were collected to determine the associated biochemical and molecular mechanisms that are activated, induced or augmented by the experimental interventions tested.

Male Golden Syrian Hamsters were purchased from Charles River Co. housed individually in cages for two weeks prior to the commencement of the study. During this adjustment period, animals were fed with regular rodent chow diet with free access to both food and water. A total of 60 hamsters were weighed and randomly assigned to one of four groups of 15 animals each. Animals are subjected to a temperature-controlled environment with a 12:12 h light/dark cycle. Each group was fed with one of the four isocaloric experimental diets for a 4 week period. A preliminary study demonstrated that the addition of BBRCl to the chow does not induce a taste aversion effect as a food switch from the control diet to one containing 100 mg/kg BBRCl did not change the food intake. During the course of the experiment, animals were weighed weekly and food consumption was determined on a daily basis over the course of the experiment.

At the conclusion of the study all animals were anaesthetized with isoflurane and killed by decapitation. Blood samples were collected into tubes containing ethylenediaminetetraacetic acid (EDTA). Red blood cells and plasma were separated and stored at −80° C. until further analysis. Plasma was analyzed for total cholesterol, HDL-C and TG concentrations, for which results are reported below. Non-HDL-C was calculated by subtracting HDL-C from total cholesterol.

Figure 1:
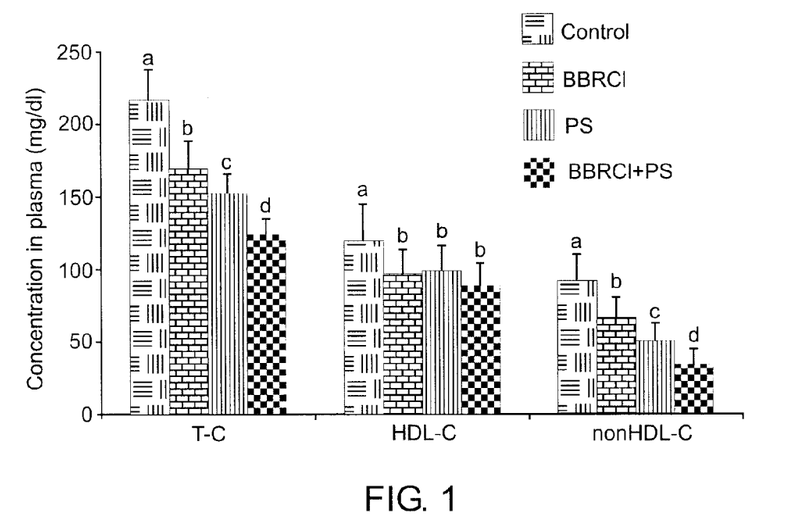
FIG. 1 is a graph depicting effect of berberine chloride and plant stanols on circulating cholesterol levels in hamsters fed an atherogenic control diet and the atherogenic control diet supplemented with berberine chloride and/or plant stanols for 4 weeks (for each lipid parameter, values with different superscripts (a, b, c or d) are significantly different)
Figure 2:
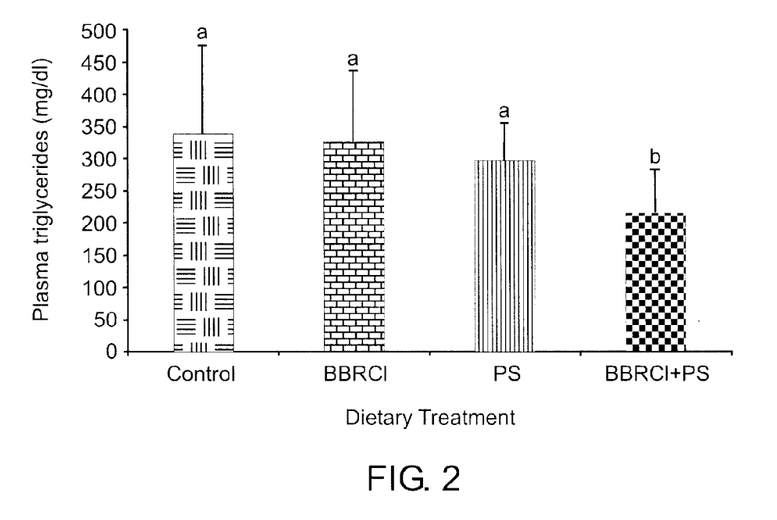
FIG. 2 is a graph depicting effect of berberine chloride and plant stanols on plasma triglyceride concentration in hamsters fed an atherogenic control diet and the atherogenic control diet supplemented with berberine chloride and/or plant stanols for 4 weeks (values with different superscripts (a or b) are significantly different)
Figure 3:
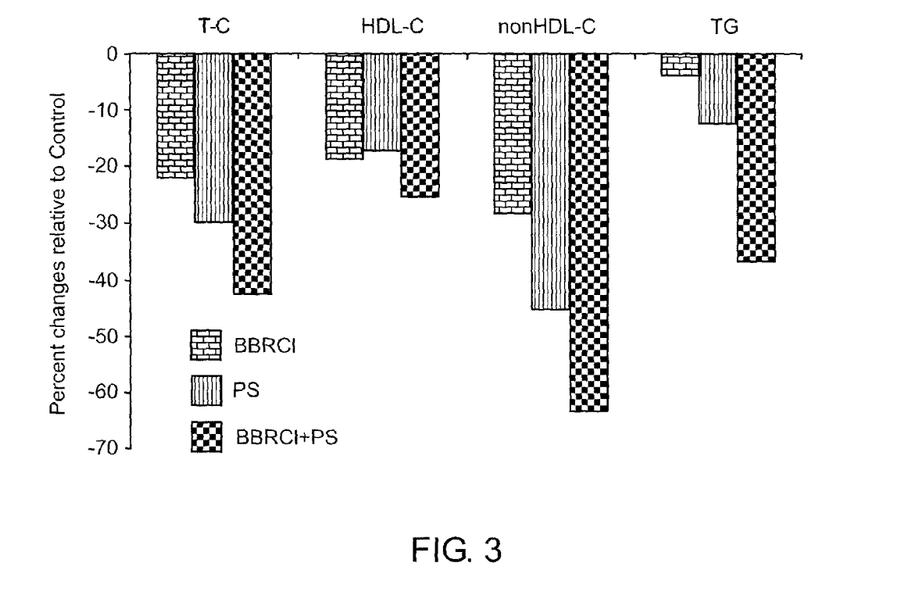
FIG. 3 is a graph depicting percent changes of plasma cholesterol and triglyceride concentration in hamsters fed an atherogenic control diet and the atherogenic control diet supplemented with berberine chloride and/or plant stanols.

FIGS. 1-3 and Table 2 represent the effects of BBRCl and PS alone or in combination on blood cholesterol and triglyceride levels. Values are means±SD, n=15. Data were analyzed by one-way ANOVA followed by Tukey test if significance was detected. A significant difference was indicated by a $p<0.05$.

The results obtained strongly support that BBRCl and the combination of BBRCl with plant stanols (for this example) induces a beneficial effect on blood lipid profiles (see FIGS. 1-3 and Table 2). The results showed a novel and very important finding that dietary supplementation of BBRCI and plant stanols acted synergistically to lower circulating TG levels (see FIG. 2), whereas neither BBRCI (100 mg/kg·d) alone nor plant stanols (1% (w/w)) alone showed any significant reduction of TG levels (BBRCI reduced TG by only 4% and PS reduced TG by 11%). When BBRCI and PS were combined together, plasma TG levels in this group of 15 animals decreased by an average of 36%. Moreover, both materials showed significant effects in lowering T-C and nonHDL-C levels (see FIG. 1).

TABLE 2

|  | T-C | HDL-C | nonHDL-C | HDL-C/nonHDL-C | TG |
|---|---|---|---|---|---|
| Concentration (mg/dl) | | | | | |
| Control | $217 \pm 21^a$ | $119 \pm 26^a$ | $92 \pm 17^a$ | $1.35 \pm 0.46^b$ | $339 \pm 137^a$ |
| BBRCI | $169 \pm 20^b$ | $100 \pm 17^b$ | $66 \pm 14^b$ | $1.60 \pm 0.58^b$ | $326 \pm 111^a$ |
| PS | $152 \pm 14^c$ | $99 \pm 18^b$ | $51 \pm 21^c$ | $2.21 \pm 1.34^{ab}$ | $297 \pm 58^a$ |
| BBRCI + PS | $125 \pm 11^d$ | $89 \pm 15^b$ | $34 \pm 11^d$ | $3.10 \pm 1.82^a$ | $215 \pm 68^b$ |
| % difference from Control | | | | | |
| Control | 0 | 0 | 0 | 0 | 0 |
| BBRCI | −21.9 | −16.2 | −28.2 | 19 | −3.9 |
| PS | −29.8 | −17.2 | −45.0 | 64 | −10.6 |
| BBRCI + PS | −42.5 | −25.4 | −63.2 | 130 | −36.6 |

In terms of converting the data to a more conventional reporting format where the % change of blood total and sub-fraction of cholesterol levels relative to control is calculated and presented, it was found that BBRCI reduced T-C by 22% and nonHDL-C by 28% while plant stanols reduced T-C and nonHDL-C by 30% and 45%, respectively. The combination of both materials lowered T-C by 42% and nonHDL-C by 63% (see FIG. 3). BBRCI and PS tended to improve the ratio of HDL-C to nonHDL-C. When BBRCI and PS were supplemented simultaneously in the diet, the ratio of HDL-C to nonHDL-C was improved significantly through a synergistic action mode.

Histopathological testing and examination of gross and microscopic examination of thin sections of the various organs were conducted by a certified pathologist. There were no significant changes in the appearance or weight of brain, lung, heart, spleen and kidney. However, the livers of control animals were observably yellowish and heavier than those of animals treated with BBRCI or plant stanols, or the combination of either.

Table 3 summarizes the effect of BBRCI and plant stanols on the percent tissue weight relative to body weight. For each tissue weight to body weight parameter in Table 3, values with different superscripts (a or b) are significantly different. The results suggest beneficial effects to the liver and liver function as BBRCI and PS alone and especially BBRCI and PS in combination markedly reduced the appearance of fatty liver, and significantly lowered organ weight compared to the livers of the control animals.

Figure 4:
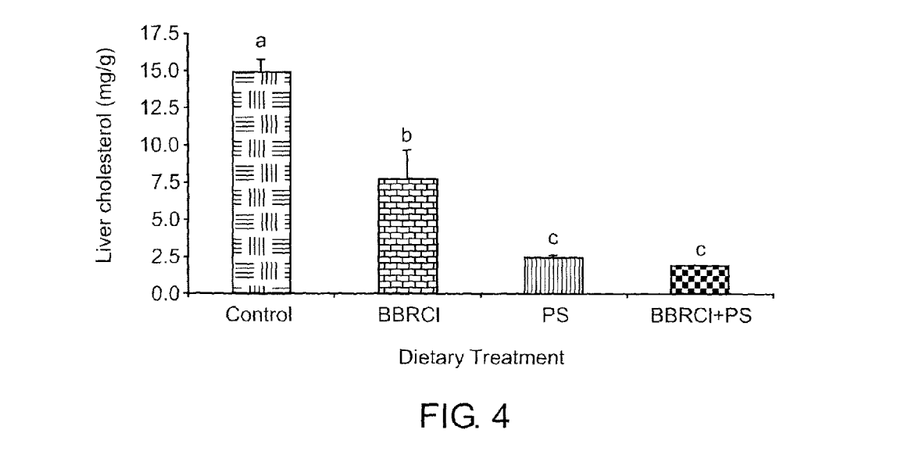
FIG. 4 is a graph depicting effect of berberine chloride and plant stanols on liver cholesterol concentration in hamsters fed an atherogenic control diet and the atherogenic control diet supplemented with berberine chloride and/or plant stanols for 4 weeks (values with different superscripts (a, b or c) are significantly different)

FIG. 4 shows the effect of BBRCI and PS alone and in combination the cholesterol content in the liver. Dietary supplementation of BBRCI and PS either alone or combined together dramatically reduced cholesterol concentration in the liver of hamsters. This observation, together with lower liver weight, implies that either BBRCI or PS or combination of either can be used to treat fatty liver.

Figure 5:
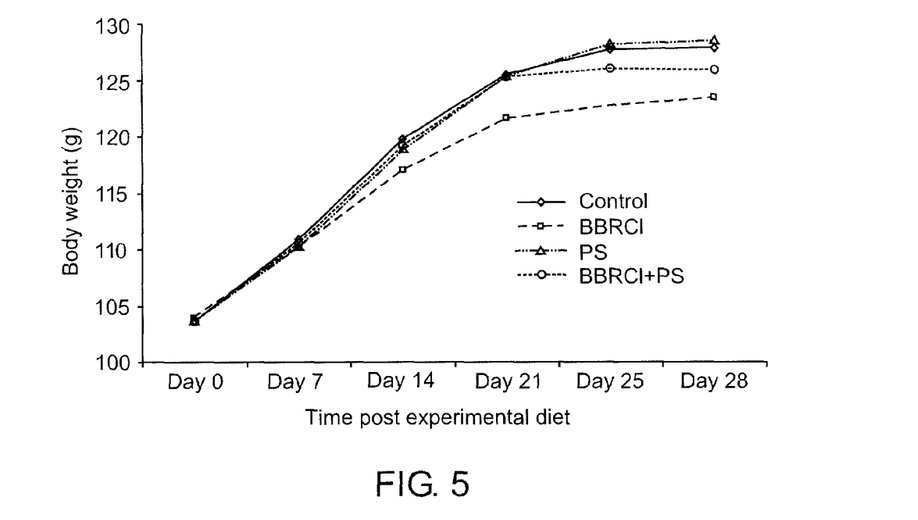
FIG. 5 is a graph depicting effect of berberine chloride and plant stanols on the weekly body weight in hamsters fed an atherogenic control diet and the atherogenic control diet supplemented with berberine chloride and/or plant stanols for 4 weeks.

During the course of the experiment, data were obtained with regard to food consumption and bodyweight so that the dose of BBRCI was maintained on a mg/kg basis as the animals grew over the 4 weeks experimental period. Data showed that the body weight and food intake were not immediately affected by the switch from the control diet to any of the three test diets used (BBRCI alone, PS alone, or BBRCI/PS combination, see FIGS. 5-6). Analysis of the data showed an unexpected trend toward reduced body weights after two weeks of feeding with BBRCI alone and after 3 weeks of feeding with BBRCI+PS combination (see FIG. 5). These results indicate that BBRCI and the combination of BBRCI and PS may be useful in weight control in addition to the beneficial effects of lipid lowering. This may have important implications on weight control, healthy weight management strategies, and body composition (increase lean body mass) in humans and animals.

Figure 6:
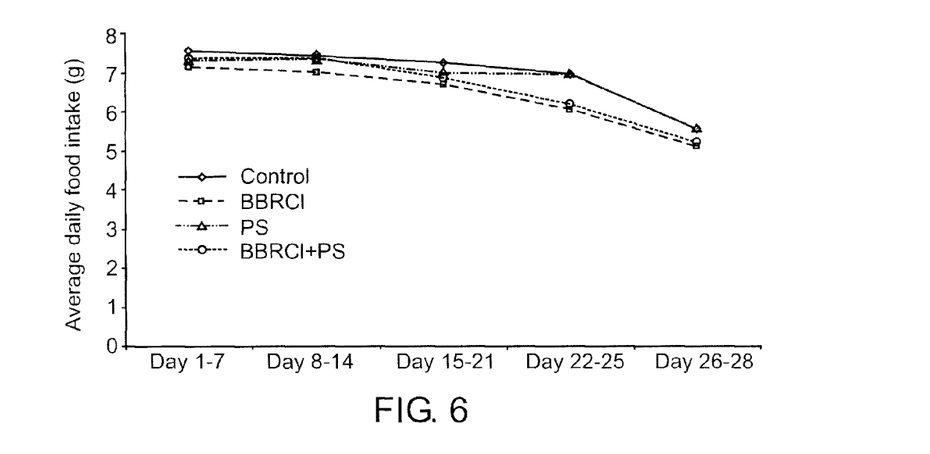
FIG. 6 is a graph depicting effect of berberine chloride and plant stanols on average daily feed intake in hamsters fed an atherogenic control diet and the atherogenic control diet supplemented with berberine chloride and/or plant stanols for 4 weeks.

Similarly, during the early segments of the experiment the daily food intake was not affected by BBRCI until after 3 weeks (see FIG. 6). Thereafter, significant differences in food intake was observed from days 22-25 but this effect disappeared during days 25-28 as a small surgical intervention was performed on each animal on day 25 on the neck area of the animal, which reduced food consumption in each treatment. Surgical intervention was performed to permit intravenous injection of a stable isotope cholesterol tracer.

The experimental results described above show that a powerful synergistic effect of BBRCI and PS on TG reduction exists. Dramatic reductions in serum T-C and nonHDL-C occurred when BBRCI and PS were combined at the levels used in these experiments.

TABLE 3

|  | Brain | Heart | Lung | Liver | Spleen | Right kidney |
|---|---|---|---|---|---|---|
| Control | $0.81 \pm 0.05$ | $0.38 \pm 0.04$ | $0.52 \pm 0.08$ | $5.0 \pm 0.04^a$ | $0.12 \pm 0.02$ | $0.34 \pm 0.02$ |
| BBRCI | $0.83 \pm 0.06$ | $0.36 \pm 0.03$ | $0.54 \pm 0.06$ | $4.4 \pm 0.4^b$ | $0.11 \pm 0.01$ | $0.32 \pm 0.03$ |
| PS | $0.79 \pm 0.06$ | $0.37 \pm 0.04$ | $0.51 \pm 0.07$ | $4.6 \pm 0.4^a$ | $0.12 \pm 0.01$ | $0.33 \pm 0.02$ |
| BBRCI + PS | $0.81 \pm 0.07$ | $0.36 \pm 0.03$ | $0.54 \pm 0.06$ | $3.9 \pm 0.3^b$ | $0.11 \pm 0.02$ | $0.33 \pm 0.02$ |

Experiments were also conducted to determine the effect on the expression of genes associated with cholesterol in the liver and intestine. Total RNA was extracted and mRNA was converted to cDNA. The mRNA expression was measured by real-time PCR with four repeats and calculated as relative expression in reference to internal control of a housekeeping gene for each sample.

Figure 7A:
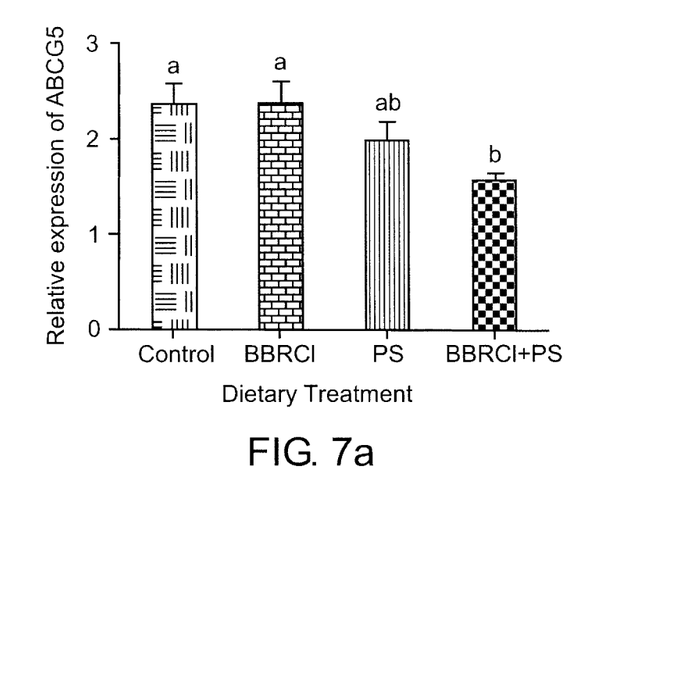
FIG. 7*a* is a graph depicting effect of berberine chloride and plant stanols on intestinal ABCG5 mRNA expression in hamsters fed an atherogenic control diet and the atherogenic control diet supplemented with berberine chloride and/or plant stanols for 4 weeks (values with different superscripts (a or b) are significantly different)
Figure 7B:
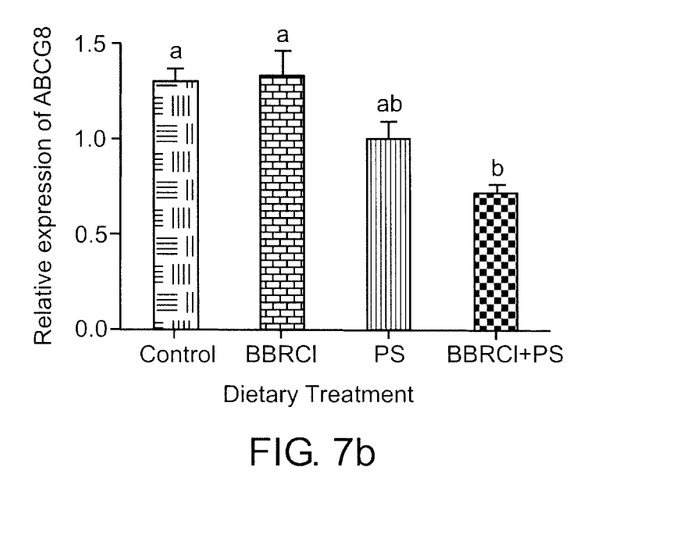
FIG. 7*b* is a graph depicting effect of berberine chloride and plant stanols on intestinal ABCG8 mRNA expression in hamsters fed an atherogenic control diet and the atherogenic control diet supplemented with berberine chloride and/or plant stanols for 4 weeks (values with different superscripts (a or b) are significantly different)

Table 4 and FIGS. 7a-7b summarize the effect of BBCI and PS alone or in combination on intestinal ABCG5 (FIG. 7a) and ABCG8 (FIG. 7b) mRNA expression. BBRCI and PS alone did not affect ABCG5 and ABCG8 mRNA expression. However, when they were administered simultaneously, the mRNA expression of both genes was significantly reduced in a synergistic mode. The function of ABCG5 and ABCG8 in the intestine is to transport cholesterol out of enterocytes and back to the intestine for elimination via the feces. Recent observations have demonstrated that the mRNA expression of ABCG5 and ABCG8 is closely and positively associated with blood cholesterol levels. When a strong action occurs on cholesterol reduction, the expressions of these two genes are down-regulated. The observation of our study (Example 1) has provided a strong support to the synergistic action of BBRCI and PS on cholesterol reduction.

TABLE 4

|  | ABCG5 | ABCG8 |
| --- | --- | --- |
| Control | $2.36 \pm 0.72^a$ | $1.30 \pm 0.25^a$ |
| BBRCl | $2.37 \pm 0.70^a$ | $1.33 \pm 0.45^a$ |
| PS | $1.97 \pm 0.72^{ab}$ | $0.99 \pm 0.32^{ab}$ |
| BBRCl + PS | $1.55 \pm 0.29^b$ | $0.69 \pm 0.17^b$ |

Figure 8A:
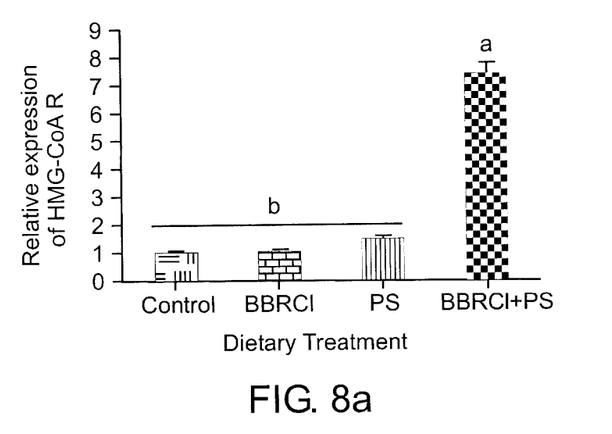
FIG. 8*a* is a graph depicting effect of berberine chloride and plant stanols on liver HMG-CoA reductase mRNA expression in hamsters fed an atherogenic control diet and the atherogenic control diet supplemented with berberine chloride and/or plant stanols for 4 weeks (values with different superscripts (a or b) are significantly different)

Table 5 and FIG. 8a summarize the effect of BBRCI and PS alone or in combination on liver HMG-CoA reductase. BBRCI and PS alone did not affect HMG-CoA reductase mRNA expression. However, when they were combined, the mRNA expression of HMG-CoA reductase was increased by 7-fold. HMG-CoA reductase is a rate-limiting enzyme in cholesterol biosynthesis. A large body of evidence has indicated that cholesterol synthesis is altered reciprocally with cholesterol absorption. When a strong action occurs on cholesterol reduction through inhibiting cholesterol absorption, cholesterol biosynthesis is increased as compensatory response to the cholesterol loss due to the reduced absorption. The powerful synergistic action of BBRCI and PS on HMG-CoA reductase mRNA expression implies that the combination of these materials may act synergistically to reduce blood cholesterol, possibly by inhibiting cholesterol absorption.

Figure 8B:
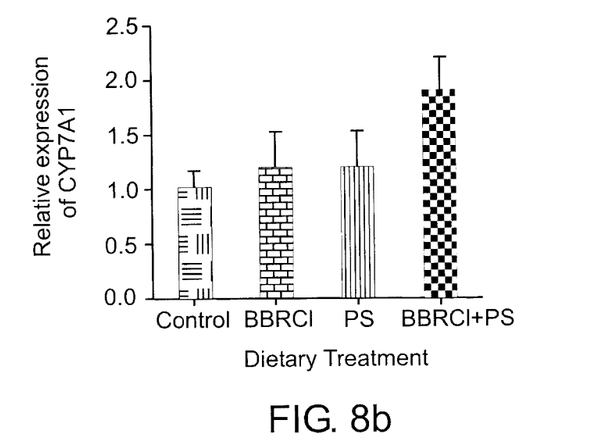
FIG. 8*b* is a graph depicting effect of berberine chloride and plant stanols on liver CYP7A1 mRNA expression in hamsters fed an atherogenic control diet and the atherogenic control diet supplemented with berberine chloride and/or plant stanols for 4 weeks; and, FIG. 8*c* is a graph depicting effect of berberine chloride and plant stanols on liver CYP27A1 mRNA expression in hamsters fed an atherogenic control diet and the atherogenic control diet supplemented with berberine chloride and/or plant stanols for 4 weeks.
Figure 8C:
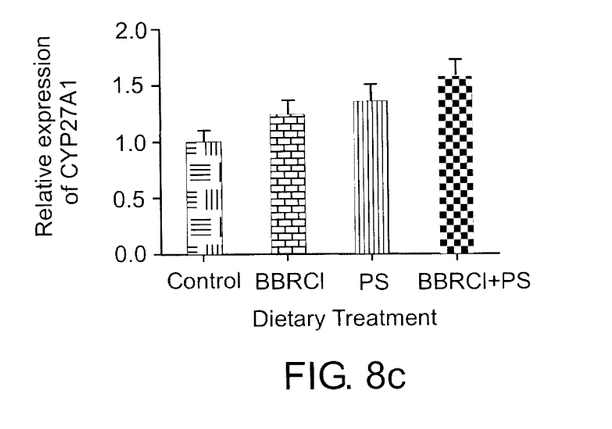

Table 5, FIG. 8b and FIG. 8c summarize the effect of BBRCI and PS on the mRNA expression of CYP7A1 and CYP27A1 in the liver. BBRCI and PS alone tended to increase mRNA expression of both genes. CYP7A1 and CYP27A1 are two rate-limiting enzymes controlling bile acid synthesis, which is one mechanism through which the body removes cholesterol by converting it into bile acids. When BBRCI and PS were combined, a synergistic action appeared to happen. This result implies that BBRCI and PS reduce blood cholesterol by affecting cholesterol catabolism in the liver through a synergistic action mode.

TABLE 5

|  | HMG-CoA reductase | CYP7A1 | CYP27A1 |
| --- | --- | --- | --- |
| Control | $1.01 \pm 0.19^b$ | $1.03 \pm 0.44$ | $1.06 \pm 0.27$ |
| BBRCl | $0.98 \pm 0.10^b$ | $1.30 \pm 0.66$ | $1.27 \pm 0.31$ |
| PS | $1.34 \pm 0.48^b$ | $1.32 \pm 0.67$ | $1.40 \pm 0.37$ |
| BBRCl + PS | $7.52 \pm 2.60^a$ | $1.83 \pm 1.05$ | $1.60 \pm 0.75$ |

There is a balance between synthesis and clearance of cholesterol in the body. Despite efficient clearance of cholesterol, the body will compensate to try to maintain a certain baseline cholesterol level. In Example 1, the strong action of the combination of BBRCI and PS may have reduced cholesterol levels to a near minimum or base level. In such a case, no observable synergistic effect is expected even though a synergistic action was implied by the gene expressions. For this reason, a synergistic action on cholesterol reduction was not detected in Example 1 as a maximum or near maximum reduction in blood lipids was achieved. Accordingly, if a sufficiently higher blood cholesterol level is achieved by increasing dietary cholesterol intake and/or if sufficiently less BBRCI and/or PS are used in the diet, a synergistic action of cholesterol reduction should be observable. Examples 2 and 3 below describe such studies.

Example 2

In this example, a controlled, five week animal study was performed. A total of 48 male Golden Syrian hamsters were randomized into 4 groups of 12 and fed isocaloric diets as follows. Hamster husbandry, living and feeding conditions were similar to that used for Example 1.

Control a semi-synthetic casein-corn starch-sucrose diet that contained 0.25% (w/w) cholesterol
BBRCI control diet containing 100 mg/kg·d of BBRCI
PS control diet containing 1% (w/w) PS
BBRCI+PS control diet containing 100 mg/kg·d BBRCI and 1% (w/w) PS One objective of this example was to determine the effects of each intervention on circulating blood lipids including total cholesterol (T-C), high-density-lipoprotein cholesterol (HDL-C), nonHDL-C (which is indicative of LDL-C levels) and triglyceride (TG) profiles when hamsters were fed a diet containing a higher concentration of cholesterol, for example, 0.25% by weight in the diet.

Table 6 summarizes the effect on blood lipid levels (values are means±SD, n=12). Data were analyzed by one-way ANOVA followed by Tukey test if significance was detected. A significant difference was indicated by a p<0.05. Values with different superscripts (a, b or c) within a specific lipid group are significantly different.

Results of this study indicate that BBRCI and PS synergistically decrease blood TG levels. BBRCI and PS did not show a synergistic action on cholesterol reduction. However, as discussed in Example 1, the reason for this may still be that the very strong cholesterol lowering action of combined BBRCI and PS was maximized under the experimental conductions (i.e. baseline levels of cholesterol were reached). Animals in Example 2 were heavier and supplemented with a higher level of dietary cholesterol in a longer feeding period than those in Example 1. As can be seen in Example 3 below, a synergistic effect on cholesterol lowering is observed when the level of cholesterol is sufficiently high and the amount of PS supplemented in the diet is reduced by 50%. The ratio of HDL-C to nonHDL-C tended to increase by BBRCI or PS alone. The combination of BBRCI and PS significantly increased the ratio of HDL-C to nonHDL-C.

TABLE 6

| | T-C | HDL-C | nonHDL-C | HDL-C/ nonHDL-C | TG |
|---|---|---|---|---|---|
| | Concentration (mg/dl) | | | | |
| Control | 287.2 ± 39.3$^a$ | 91.5 ± 20.1$^{ab}$ | 195.2 ± 46.1$^a$ | 0.51 ± 0.20$^b$ | 550.3 ± 224.9$^a$ |
| BBRCI | 264.7 ± 49.8$^a$ | 93.1 ± 27.1$^{ab}$ | 173.5 ± 66.5$^a$ | 0.66 ± 0.41$^{ab}$ | 549.1 ± 225.3$^a$ |
| PS | 180.2 ± 28.2$^{bc}$ | 77.2 ± 13.7$^b$ | 103.4 ± 27.2$^b$ | 0.84 ± 0.44$^{ab}$ | 369.6 ± 137.3$^{ab}$ |
| BBRCI + PS | 160.9 ± 23.8$^c$ | 76.3 ± 15.7$^b$ | 84.6 ± 25.3$^b$ | 1.00 ± 0.49$^a$ | 310.3 ± 127.3$^b$ |
| | % difference from Control | | | | |
| Control | 0 | 0 | 0 | 0 | 0 |
| BBRCI | −7.8 | 1.7 | −11.1 | 29 | −0.2 |
| PS | −37.3 | −15.6 | −47.0 | 65 | −32.8 |
| BBRCI + PS | −44.0 | −15.6-16.6 | −56.7 | 96 | −43.6 |

Table 7 summarizes the effect on tissue weight to body weight ratio (values are means±SD). Data were analyzed by one-way ANOVA followed by Tukey test when a significant treatment effect was detected. A significant difference was indicated by a p<0.05. Values with different superscripts (a, b or c) for each tissue weight to body weight parameter within a tissue group are significantly different. The average liver weight was statistically lower in the PS group compared to the Control group but was not significantly lower when comparing the BBRCI group with Control. The combination of BBRCI and PS (BBRCI+PS), however, reduced the average liver weight in a strong, statistically significant, and synergistic manner compared to liver weights in the BBRCI and PS groups. The BBRCI+PS induced effect on the average liver weight was also significantly lower than in Control.

TABLE 7

| | Heart | Liver | Right kidney |
|---|---|---|---|
| Control (n = 12) | 0.37 ± 0.05 | 5.03 ± 0.29$^a$ | 0.35 ± 0.04 |
| BBRCI (n = 12) | 0.37 ± 0.03 | 4.67 ± 0.38$^{ab}$ | 0.35 ± 0.03 |
| PS (n = 12) | 0.37 ± 0.03 | 4.56 ± 0.37$^b$ | 0.36 ± 0.03 |
| BBRCI + PS (n = 12) | 0.35 ± 0.04 | 3.94 ± 0.33$^c$ | 0.35 ± 0.03 |

Example 3

In this example, a controlled, five week animal study was performed. Four randomized groups of 12 or 6 male Golden Syrian hamsters were fed isocaloric diets as follows. The dosage of PS was reduced from 1% to 0.5% (w/w) in the diet. Hamster husbandry, living and feeding conditions were similar to that in Example 1.

Control a semi-synthetic casein-corn starch-sucrose diet that contained 0.25% (w/w) cholesterol BBRCI control diet containing 100 mg/kg·d of BBRCI PS control diet containing 0.5% (w/w) PS BBRCI+PS control diet containing 100 mg/kg·d BBRCI and 0.5% (w/w) PS One objective of this example was to determine the effects of each intervention on circulating blood lipids including total cholesterol (T-C), high-density-lipoprotein cholesterol (HDL-C), nonHDL-C (which is indicative of LDL-C levels) and triglyceride (TG) profiles.

Table 8 summarizes the effect on blood lipid levels (values are means±SD, n=12). Data were analyzed by one-way ANOVA followed by Tukey test if significance was detected. A significant difference was indicated by a p<0.05. Values with different superscripts (a, b or c) within a specific lipid group are significantly different. When BBRCI and PS were given to hamsters simultaneously, significant synergistic actions were observed on T-C, nonHDL-C and TG levels. A synergistic action of BBRCI and PS was also observed on the ratio of HDL-C and nonHDL-C. It has been demonstrated by the results of this study that BBRCI and PS act synergistically to reduce blood total cholesterol, nonHDL-C and triglyceride levels.

TABLE 8

| | T-C | HDL-C | nonHDL-C | HDL-C/ nonHDL-C | TG |
|---|---|---|---|---|---|
| | Concentration (mg/dl) | | | | |
| Control | 287.2 ± 39.3$^a$ | 91.5 ± 20.1 | 195.2 ± 46.1$^a$ | 0.51 ± 0.20$^b$ | 550.3 ± 224.9$^a$ |
| BBRCI | 264.7 ± 49.8$^a$ | 93.1 ± 27.1 | 173.5 ± 66.5$^{ab}$ | 0.66 ± 0.41$^b$ | 549.1 ± 225.3$^a$ |
| PS | 212.1 ± 20.3$^b$ | 108.2 ± 19.1 | 111.2 ± 19.0$^{bc}$ | 1.02 ± 0.37$^{ab}$ | 341.4 ± 121.7$^{ab}$ |
| BBRCI + PS | 164.3 ± 17.5$^b$ | 98.5 ± 12.7 | 65.9 ± 12.3$^c$ | 1.56 ± 0.47$^a$ | 278.2 ± 89.9$^b$ |
| | % difference from Control | | | | |
| Control | 0 | 0 | 0 | 0 | 0 |
| BBRCI | −7.8 | 1.7 | −11.1 | 29 | −0.2 |
| PS | −26.2 | 18.3 | −43.0 | 100 | −37.9 |
| BBRCI + PS | −42.8 | 7.7 | −66.2 | 206 | −49.5 |

Example 4

In this example, a controlled, six week animal study was performed in a different animal model. Six randomized groups of 10 male Sprague-Dawley rats were fed isocaloric diets as follows. The PS was introduced into the diet by blending and BBRCI was introduced by gavage feeding twice a day.

Control a semi-synthetic casein-corn starch-sucrose diet that contained 2% (w/w) cholesterol and 28% (w/w) fat
BBRCI-1 control diet containing 100 mg/kg·d of BBRCI
PS control diet containing 1% (w/w) PS
BBRCI-1+PS control diet containing 100 mg/kg·d BBRCI and 1% (w/w) PS
BBRCI-2 control diet containing 200 mg/kg·d of BBRCI
BBRCI-2+PS control diet containing 200 mg/kg·d BBRCI and 1% (w/w) PS One objective of this example was to determine the effects of each intervention on plasma cholesterol levels in a different animal model.

Table 9 summarizes the effect on blood total cholesterol levels (values are means±SD, n=10). A significant synergistic total cholesterol reduction was seen for the combination of either of two doses of BBRCI and PS. Results of this study demonstrate in a different animal model that BBRCI and PS synergistically reduce blood total cholesterol levels.

TABLE 9

|  | T-C (mg/dl) |
|---|---|
| Control | 109.4 ± 22.8 |
| BBRCl-1 | 102.1 ± 30.6 |
| PS | 90.0 ± 29.0 |
| BBRCl-1 + PS | 67.2 ± 14.8 |
| BBRCl-2 | 109.1 ± 26.7 |
| BBRCl-2 + PS | 83.1 ± 18.1 |

|  | % difference from Control |
|---|---|
| Control | 0 |
| BBRCl-1 | −6.7 |
| PS | −17.8 |
| BBRCl-1 + PS | −38.6 |
| BBRCl-2 | −0.3 |
| BBRCl-2 + PS | −24.0 |

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of lowering blood lipid levels in a mammal in need thereof comprising administering a blood lipid level lowering combination of:
   - 5 mg or more per kg of body weight per day of berberine, one or more of pharmacologically acceptable salts thereof, or a mixture thereof;
   - 5 mg or more per kg of body weight per day of a Blood Lipid Lowering Agent (BLLA), wherein the BLLA is a plant sterol, a plant stanol, an ester of a plant sterol, an ester of a plant stanol, or a mixture thereof;
   - wherein the combination lowers a blood lipid level by an amount that is more than, and that has a statistically significant difference over, an amount expected from adding separate blood lipid lowering effects of BBR and BLLA, and wherein the statistically significant difference is indicated by a p value of less than 0.05 in an ANOVA test.

2. The method of claim 1, further comprising administering Red Yeast Rice.

3. The method of claim 1, wherein administering said is accomplished orally.

4. The method of claim 1, wherein the blood lipid levels that are lowered comprise triglyceride levels.

5. The method of claim 1, wherein the blood lipid levels that are lowered comprises low-density-lipoprotein cholesterol levels.

6. The method of claim 1, wherein the blood lipid levels that are lowered comprises total cholesterol levels.

7. The method of claim 1, wherein the mammal is a human, dog, cat or horse.

8. The method of claim 1, wherein the combination comprises an omega-3 fatty acid ester of a plant sterol or plant stanol.

9. The method of claim 1, wherein the berberine, pharmacologically acceptable salt thereof or mixture thereof is administered in a daily amount of 50 mg or more per kg of body weight and the plant sterol, plant stanol, ester of a plant sterol, ester of a plant stanol or mixture thereof is administered in a daily amount of 50 mg or more per kg of body weight.

10. The method of claim 1, wherein administration of the combination is effective for treating fatty liver.

11. The method of claim 1, wherein administration of the combination is effective for lowering weight of the mammal.

* * * * *